United States Patent [19]

Brunner et al.

[11] Patent Number: 4,959,205
[45] Date of Patent: Sep. 25, 1990

[54] COMPOSITION AND METHOD FOR TREATMENT OF DERMAL INFLAMMATION

[75] Inventors: Maureen Brunner, San Francisco; Howard Palefsky, Atherton, both of Calif.

[73] Assignee: Collagen Corporation, Palo Alto, Calif.

[21] Appl. No.: 327,488

[22] Filed: Mar. 23, 1989

[51] Int. Cl.$^5$ .................. A61K 7/40; A61K 7/42; A61K 31/56
[52] U.S. Cl. ...................... 424/59; 514/177; 514/847; 514/886; 514/887; 514/938
[58] Field of Search ............... 424/59; 514/887

[56] References Cited

U.S. PATENT DOCUMENTS

| | | | |
|---|---|---|---|
| 4,083,974 | 4/1978 | Turi | 424/81 |
| 4,098,881 | 7/1978 | Majeti | 424/59 |
| 4,185,100 | 1/1980 | Rovee et al. | 514/887 UX |
| 4,199,576 | 4/1980 | Reller et al. | 514/887 |
| 4,244,970 | 1/1981 | Dewhirst | 514/887 |
| 4,435,390 | 3/1984 | Annen et al. | 514/887 |
| 4,738,956 | 4/1988 | Scott et al. | 424/DIG. 5 |

FOREIGN PATENT DOCUMENTS 1539625  6/1976  United Kingdom .

OTHER PUBLICATIONS

The Merck Index, 1976, 9th edition, pp. 629 and 630.
B. Ljunggren et al, *Arch Derm Forsch* (1973) 248:1–12.
J. P. Callen et al, *Arthritis Rheum* (Aug. 1988) 31:1007–13.
L. H. Kligman, *J Invest Dermatol* (1987) 88:12s–17s.
A. D. Pearse et al, *J Invest Dermatol* (1987) 88:83–87.
M. Pathak, *Dermatologic Clin* (1986) 4:321–34 (Pathak I).
M. Pathak et al, *J Amer Acad Dermatol* (1986) 15:894–99.
T. Schwartz et al, *Dermatologica* (1985) 171:450–58.
L. E. Gibson et al, *Geriatrics* (1985) 40:87–92.
K. Kyuki et al, *Jap J Pharmacol* (1983) 33:121–32.
M. Pathak, *J Amer Acad Dermatol* (1982) 7:285–312.
P. Peters et al, *Agents & Actions* (1977) 7:545–53.

*Primary Examiner*—Dale R. Ore
*Attorney, Agent, or Firm*—Irell & Manella

[57] ABSTRACT

Mild dermal inflammation, such as mild eczema and seborrhea, is treated by daily application of a composition comprising 0.25%–0.5% hydrocortisone, a protective amount of a sunscreen agent, and a pharmaceutically acceptable carrier.

6 Claims, No Drawings

COMPOSITION AND METHOD FOR TREATMENT OF DERMAL INFLAMMATION

DESCRIPTION

1. Technical Field

This invention is in the field of topical treatment of dermal inflammation, and protective and therapeutic compositions therefore.

2. Background of the Invention

It is now believed that chronic exposure to sunlight is detrimental to human skin. Although exposure typically effects a tan, having a healthy appearance, it is now known that the tanning process damages the skin. In mild cases, this damage may cause dermatoheliosis, resulting in excessive creasing and wrinkling of the dermis, irregular thickening and thinning, yellowing and drying, and macular hyperpigmentation and hypopigmentation: in short, "premature aging." Crosslinking of collagen and elastic fibers is also observed, leading to alteration of connective tissue and loss of elasticity. More extreme exposures may cause acute erythema and inflammation (e.g., sunburn), and over chronic or repeated occurrence may lead to keratoses, precancerous and cancerous lesions of the skin (e.g., cheilitis, basal cell carcinoma, squamous cell carcinoma, melanoma), alteration of the immune response, and other effects. Most damage caused by sunlight is attributed to uv radiation in the wavelength range of 290–320 nm ("uvB"), which is capable of causing dimer formation in DNA bases, and free radical formation in the skin, which may lead to cross-linking of connective tissue fibers and other distortions. However, it has also been reported that uvA (320–400 nm) is capable of causing reactions in the dermis, and possibly the epidermis.

Protection from damage due to sunlight traditionally comprises clothing over most of the body, with occasional application of a sunscreen or sunblock formulation ("suntan lotion") during periods of greater exposure. Sunscreens are chemicals which absorb uv radiation in the hazardous wavelength range, and are generally water-soluble. Sunscreens generally absorb only a fraction of the incident uv radiation, and allow some uv to pass through. The proportion of uv absorbed is reported as the "sun protection factor" or spf, and indicates the factor by which one may increase one's exposure to sunlight without burning. In contrast, a sunblock is generally an opaque formulation, typically containing titanium dioxide or zinc oxide, which stops essentially all light from reaching the skin. However, the face and hands are typically left unprotected on a daily basis.

M. Pathak, *Dermatologic Clin* (1986) 4:321–34 disclosed various sunscreen agents and formulations, and the effects of uv radiation on skin. Pathak suggested using sunscreen formulations of at least spf 6–10 on a daily basis, using spf 15 when working or exercising outdoors.

L. E. Gibson et al, *Geriatrics* (1985) 40:87–92 disclosed precancerous inflammations of the lip which are caused by long-term exposure to sunlight. Suggested treatments for chronic actinic cheilitis included sun protection using hats or opaque sunscreens (such as $Ti_2$ or ZnO), and topical hydrocortisone cream. The treatment prescribed for acute actinic cheilitis was application to the lips of sunblocking ointments or pastes and 1% hydrocortisone.

P. Peters et al, *Agents & Actions* (1977) 7:545–53 disclosed the prophylactic and therapeutic abilities of various compounds to reduce erythema (redness) induced by exposure to uv light. Hydrocortisone at 1% (in 70% EtOH) failed to provide any protection when administered 30 minutes prior to uv exposure. Hydrocortisone at 10% in mineral oil provided moderate, statistically significant protection. PABA at 5% in 50% ethanol failed to provide protection, but was moderately protective when administered at 5% or 10% in 70% EtOH, or at 10% in mineral oil. Neither hydrocortisone nor PABA demonstrated therapeutic activity (i.e., no protection when applied after uv exposure).

T. Schwarz et al, *Dermatologica* (1985) 171:450–58 disclosed the ability of indomethacin (a non-steroidal antiinflammatory compound) to act as both a true sunscreen, and as a therapeutic antiinflammatory agent in sunburn. Indomethacin was able to actually filter uv light.

K. Kyuki et al, *Jap J Pharmacol* (1983) 33:121–32 disclosed topical formulations of the non-steroidal anti-inflammatory drugs indomethacin, diclofenac sodium, and bufexamac, and disclosed their ability to inhibit uv-induced erythema.

Vanlerberghe et al, GB 1,539,625, disclosed liposomal compositions for treating skin. Vanlerberghe mentioned that the compositions may contain, amongst a large number of other possible ingredients, water-soluble agents for protecting against sunburn and anti-inflammatory agents including hydrocortisone.

Turi, U.S. Pat. No. 4,083,974 disclosed topical formulations of antiinflammatory steroids using polyoxypropylene 15 stearyl ether.

DISCLOSURE OF THE INVENTION

I have now invented a topical composition which is surprisingly effective for treatment of dermal inflammation, and prophylaxis against premature skin aging. The composition comprises a low dosage of hydrocortisone in combination with a water-soluble sunscreen agent. The composition is suitable for daily application.

Another aspect of the invention is the method for treating dermal inflammation and prevention of premature aging by topical application of the composition of the invention.

MODES OF CARRYING OUT THE INVENTION

A. Definitions

The term "sunscreen" as used herein refers to the compounds para-aminobenzoic acid (PABA), amyldimethyl-para-aminobenzoic acid, octyldimethyl-para-aminobenzoic acid, glyceryl-para-aminobenzoic acid, 2-ethylhexyl-4-dimethylaminobenzoate (padimate), oxybenzone, dioxybenzone, 3,3,5-trimethylcyclohexylsalicylate (homosalate), 2-ethoxyethyl-p-methoxycinnamate (cinoxate), digalloyl trioleate, methyl anthranilate, octylmethoxycinnamate, 2-phenylbenzimidazole-5-sulfonic acid, 2-phenyl-t-methoxybenzophenone, 4-t-butyl-4'-methoxydibenzoylmethane, and octyl salicylate. The presently preferred sunscreens are octyl salicylate and octylmethoxycinnamate.

The term "dermal inflammation" refers to mild skin disorders including dryness, mild seborrhea, mild eczema, and related conditions.

The term "effective amount" refers to the amount of sunscreen agent which is capable of effecting treatment of dermal inflammation when applied topically in combination with 0.25%–0.5% hydrocortisone. The precise effective amount will vary from individual to individual, but in general will be an amount equivalent to an spf of about 4–15, preferably about 5–9. Spf values greater than 15 may also be used, if desired.

The term "pharmaceutically acceptable carrier" refers to ointment bases, creams, emulsions, solutions, and the like, which are acceptable for topical application to mammalian skin.

The terms "treating" and "treatment" as used herein refer to (a) eliminating or reducing the symptoms of a disease or disorder, (b) preventing the symptoms or disorder from increasing in severity, and (c) preventing the disorder from occurring in the first instance (prophylaxis).

B. General Method

The compositions of the invention are prepared using standard manufacturing techniques for ointments and creams. In addition to 0.25%–0.5% hydrocortisone and a suitable sunscreen agent, the composition may contain moisturizers, humectants such as glycerin and propylene glycol, emollients such as cocoa butter, castor oil, theobroma oil, myristyl alcohol, and the like; keratolytics, such as benzoyl peroxide, salicylic acid, and urea; antioxidants and preservatives such as BHA, BHT, ascorbic acid and the like; fragrances; lubricants such as isopropyl myristate; emulsifiers such as triethanolamine, alginate, carrageenan, methylcellulose, polyvinyl alcohol, and the like; surfactants, such as Tween®, Arlacel®, and the like; stabilizers, and the like. Other components and techniques of preparation are described in E. W. Martin, "Remington's Pharmaceutical Sciences" (Mack Pub. Co.).

The compositions of the invention are applied to all exposed skin surfaces, particularly the face, neck, hands, and arms.

C. Examples

The examples presented below are provided as a further guide to the practitioner of ordinary skill in the art, and are not to be construed as limiting the invention in any way.

EXAMPLE 1

(Preparation of Exemplary Compositions)

(A) A hand cream suitable for daily application was prepared as follows:

| deionized water | 328.95 g |
|---|---|
| Carbopol ® 940 | 2.00 g |
| methylparaben | 1.00 g |
| propylparaben | 0.50 g |
| glycerin (96%) | 20.00 g |
| Ajidew N50 | 5.00 g |
| Germall 115 | 1.50 g |
| Tween ® 60 | 7.50 g |
| Petrolatum (UPS) | 10.00 g |
| octyl salicylate | 15.00 g |
| Arlacel ® 165 | 12.50 g |
| Arlacel ® 60 | 10.00 g |
| silicone SF96-200 | 15.00 g |
| Ceraphyl 41 | 10.00 g |
| Ceraphyl 368 | 10.00 g |
| octyl methoxycinnamate | 37.50 g |
| cetyl alcohol (95%) | 10.00 g |
| triethanolamine | 2.00 g |
| Hyladerm | 0.05 g |
| Chemoderm 1010 | 0.25 g |
| hydrocortisone (USP) | 1.25 g |

The water was heated to 75° C., and the Carbopol was dispersed in the water. Next, the methylparaben, propylparaben, glycerin, Ajidew, Germall, and Tween ® 60 were dispersed in the aqueous Carbopol ® mixture. The petrolatum, octyl salicylate, Arlacel ® 165, Arlacel ® 60, silicone, Ceraphyl 41, Ceraphyl 368, and octyl methoxycinnamate were then combined and heated to 75° C., stirring until a homogeneous mixture was obtained. The petrolatum mixture was then combined with the aqueous mixture, and the triethanolamine added and stirred. The resulting mixture was cooled to 45° C., and the Hyladerm, Chemoderm, and hydrocortisone added and stirred. The resulting cream was then packaged.

(B) A moisturizing face cream suitable for daily application was prepared as follows:

| deionized water | 334.45 g |
|---|---|
| Carbopol ® 941 | 0.50 g |
| methylparaben | 1.00 g |
| propylparaben | 0.50 g |
| glycerin (96%) | 20.00 g |
| Germall 115 | 1.50 g |
| Tween ® 60 | 7.50 g |
| Petrolatum (USP) | 10.00 g |
| octyl salicylate | 15.00 g |
| Arlacel ® 165 | 7.50 g |
| Arlacel ® 60 | 12.50 g |
| silicone SF96-200 | 10.00 g |
| mineral oil 65/75 | 15.00 g |
| Parsol MCX | 37.50 g |
| Ceraphyl ® 368 | 10.00 g |
| triethanolamine | 0.50 g |
| Hyladerm | 0.05 g |
| Chemoderm 1010 | 0.25 g |
| hydrocortisone (USP) | 1.25 g |

The water was heated to 75° C., and the Carbopol ® dispersed in the water. Next, the methylparaben, propylparaben, glycerin, Germall, and Tween ® 60 were dispersed in the aqueous Carbopol ® mixture. The petrolatum, octyl salicylate, Arlacel ® 165, Arlacel ® 60, silicone, Ceraphyl ® 368, mineral oil, and Parsol ® MCX were then combined and heated to 75° C., stirring until a homogeneous mixture was obtained. The petrolatum mixture was then combined with the aqueous mixture, and the triethanolamine added and stirred. The resulting mixture was cooled to 45° C., and the Hyladerm, Chemoderm, and hydrocortisone added and stirred. The resulting cream was then packaged.

EXAMPLE 2

(Efficacy)

A human subject presented with a red, rashlike inflammation of both cheeks, of unknown origin. This inflammation had proven unresponsive to commercially available moisturizing lotions.

The composition described in Example 1(B) above was applied daily to one cheek, and a commercially available composition (Raintree ® moisturizer) was applied daily to the other cheek. After ten days, the The cheek treated with the composition of the invention exhibited a marked reduction in redness and inflamed appearance, whereas no improvement was detectable in the other cheek.

What is claimed:

1. A topical composition for treating dermal inflammation, comprising:
   0.25%–0.5% hydrocortisone;
   an effective protective amount of a water-soluble sunscreen agent; and
   a pharmaceutically acceptable carrier.

2. The composition of claim 1, wherein said sunscreen agent is selected from the group consisting of para-aminobenzoic acid, amyldimethyl-para-aminobenzoic acid, octyldimethyl-para-aminobenzoic acid, glyceryl-para-aminobenzoic acid, 2-ethylhexyl-4-dimethylaminobenzoate, oxybenzone, dioxybenzone, 3,3,5-trimethylcyclohexylsalicylate, 2-ethoxyethyl-p-methoxycinnamate, digalloyl trioleate, methyl anthranilate, octylmethoxycinnamate, 2-phenylbenzimidazole-5-sulfonic acid, 2-phenyl-t-methoxybenzophenone, 4-t-butyl-4,-methoxydibenzoylmethane, and octyl salicylate.

3. The composition of claim 2 wherein said sunscreen agent is a mixture of octyl salicylate and octylmethoxycinnamate.

4. A method for treating dermal inflammation in a mammal in need thereof, which method comprises:
applying an effective amount of a topical composition comprising 0.25%–0.5% hydrocortisone, an effective protective amount of water-soluble sunscreen agent, and a pharmaceutically acceptable carrier.

5. The method of claim 4 wherein said sunscreen agent is selected from the group consisting of para-aminobenzoic acid, amyldimethyl-para-aminobenzoic acid, octyldimethyl-para-aminobenzoic acid, glyceryl-para-aminobenzoic acid, 2-ethylhexyl-4-dimethylaminobenzoate, oxybenzone, dioxybenzone, 3,3,5-trimethylcyclohexylsalicylate, 2-ethoxyethyl-p-methoxycinnamate, digalloyl trioleate, methyl anthranilate, octylmethoxycinnamate, 2-phenylbenzimidazole-5-sulfonic acid, 2-phenyl-t-methoxybenzophenone, 4-t-butyl-4,-methoxydibenzoylmethane, and octyl salicylate.

6. The method of claim 5 wherein said sunscreen agent is a mixture of octyl salicylate and octylmethoxycinnamate.

* * * * *